(12) United States Patent
Hanley et al.

(10) Patent No.: US 8,657,812 B2
(45) Date of Patent: Feb. 25, 2014

(54) SIDE-FIRING LASER FIBER WITH INTERNAL BENT FIBER AND RELATED METHODS

(75) Inventors: Brian M. Hanley, Framingham, MA (US); Jessica Hixon, Watertown, MA (US); Christopher L. Oskin, Grafton, MA (US); Edward Sinofsky, Dennis, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1128 days.

(21) Appl. No.: 12/370,168

(22) Filed: Feb. 12, 2009

(65) Prior Publication Data

US 2009/0287197 A1 Nov. 19, 2009

Related U.S. Application Data

(60) Provisional application No. 61/054,274, filed on May 19, 2008.

(51) Int. Cl.
*A61B 18/18* (2006.01)

(52) U.S. Cl.
USPC .......................................................... 606/15

(58) Field of Classification Search
USPC .......................................................... 606/15
See application file for complete search history.

(56) References Cited

U.S. PATENT DOCUMENTS

| | | |
|---|---|---|
| 5,416,878 A | 5/1995 | Bruce |
| 5,487,740 A | 1/1996 | Sulek et al. |
| 5,495,541 A | 2/1996 | Murray et al. |
| 6,179,830 B1 | 1/2001 | Kokubu |
| 6,296,608 B1 | 10/2001 | Daniels et al. |
| 6,520,927 B1* | 2/2003 | Unsworth ............... 604/19 |
| 6,565,555 B1 | 5/2003 | Ryan et al. |
| 6,802,838 B2* | 10/2004 | Loeb et al. ............. 606/13 |
| 7,112,195 B2* | 9/2006 | Boll et al. .............. 606/15 |
| 7,169,140 B1 | 1/2007 | Kume |
| 7,306,588 B2* | 12/2007 | Loeb et al. ............. 606/15 |
| 2003/0199860 A1* | 10/2003 | Loeb et al. ............. 606/17 |
| 2006/0282068 A1* | 12/2006 | Griffin et al. .......... 606/13 |
| 2007/0179485 A1* | 8/2007 | Yeik et al. .............. 606/15 |
| 2007/0270788 A1* | 11/2007 | Nahen et al. ........... 606/15 |
| 2008/0281308 A1* | 11/2008 | Neuberger et al. ..... 606/15 |
| 2010/0198009 A1 | 8/2010 | Farr et al. |

* cited by examiner

*Primary Examiner* — Bill Thomson
*Assistant Examiner* — John R Downey
(74) *Attorney, Agent, or Firm* — Bookoff McAndrews, PLLC

(57) ABSTRACT

A method and an apparatus according to an embodiment includes a distal end portion of an optical fiber disposed inside a lumen defined along a curved path within a capillary. The distal end surface of the optical fiber can be substantially flush with a portion of an outside surface of the capillary that defines a transmissive portion. The distal end portion of the optical fiber and the curved path can be collectively configured to direct laser energy through the transmissive portion in a lateral or side-fired direction that is offset from a longitudinal axis or centerline of the capillary. In some embodiments, more than one optical fiber can be disposed along the curved path. In other embodiments, more than one curved path can be defined within the capillary such that a distal end portion of an optical fiber can be disposed along each of the curved paths.

24 Claims, 15 Drawing Sheets

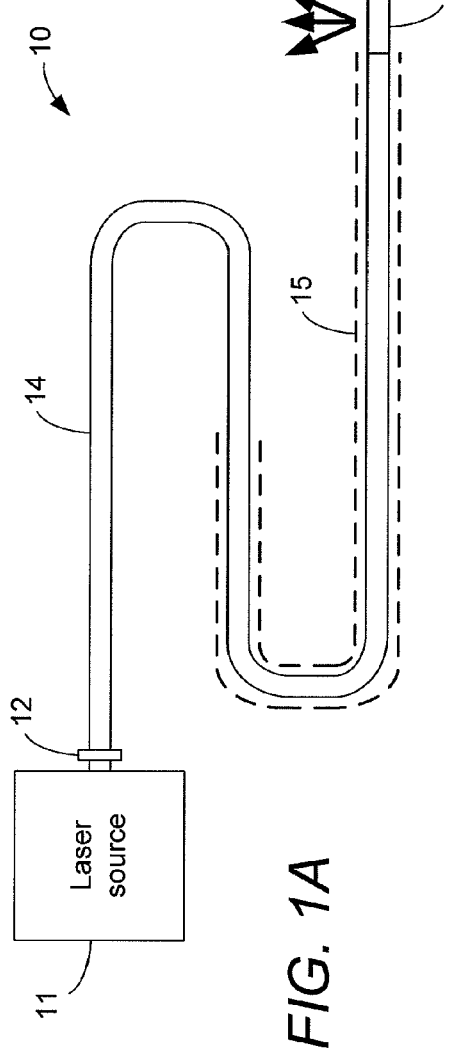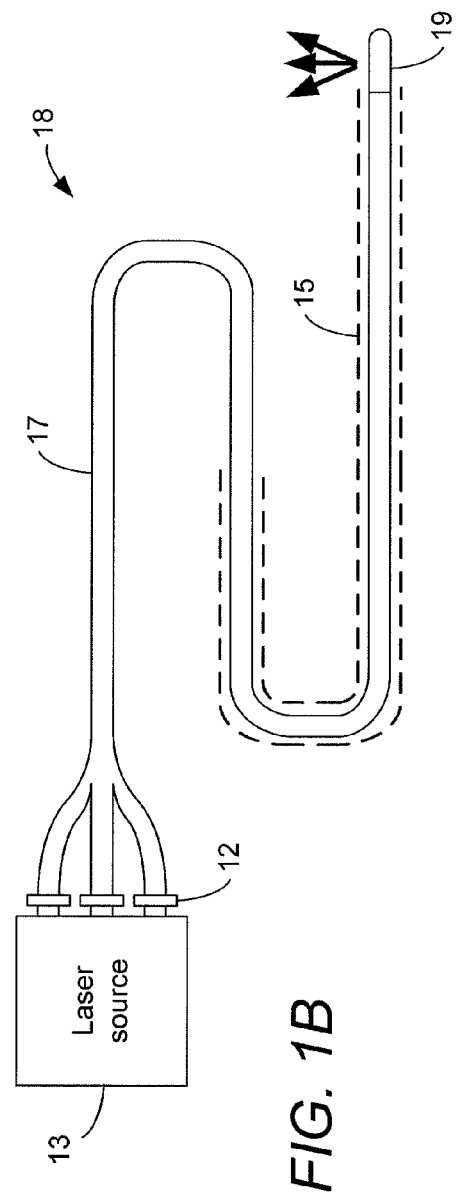
FIG. 1A
FIG. 1B

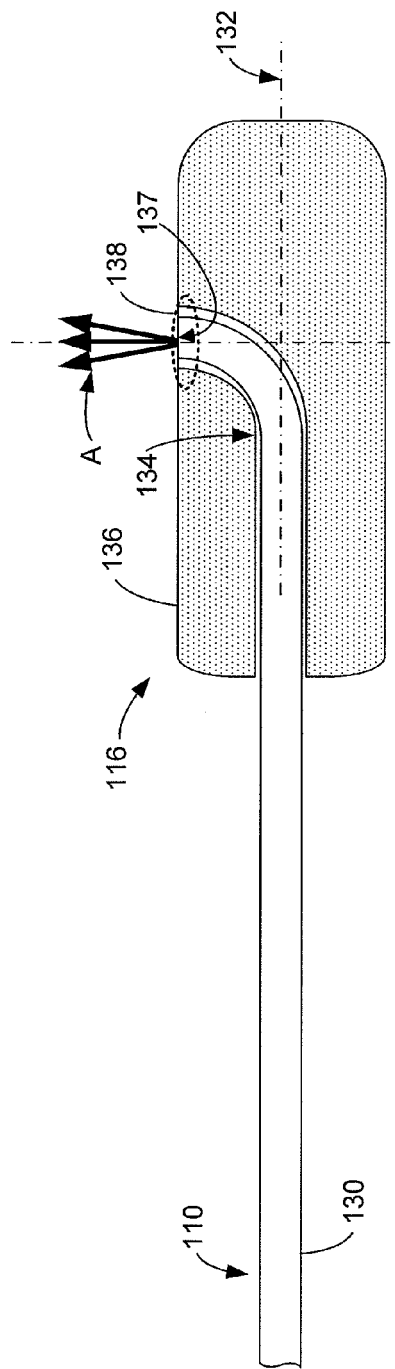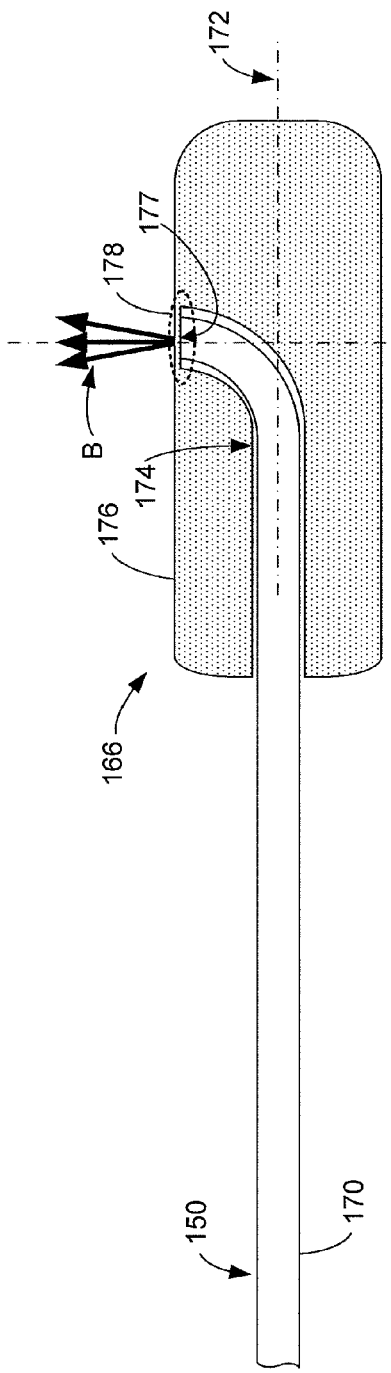
FIG. 3A
FIG. 3B

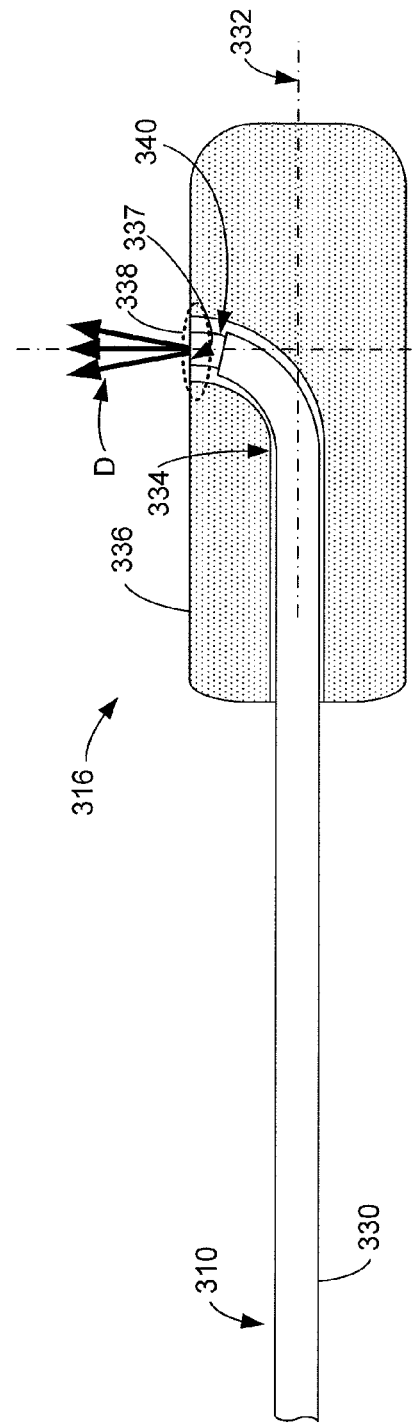
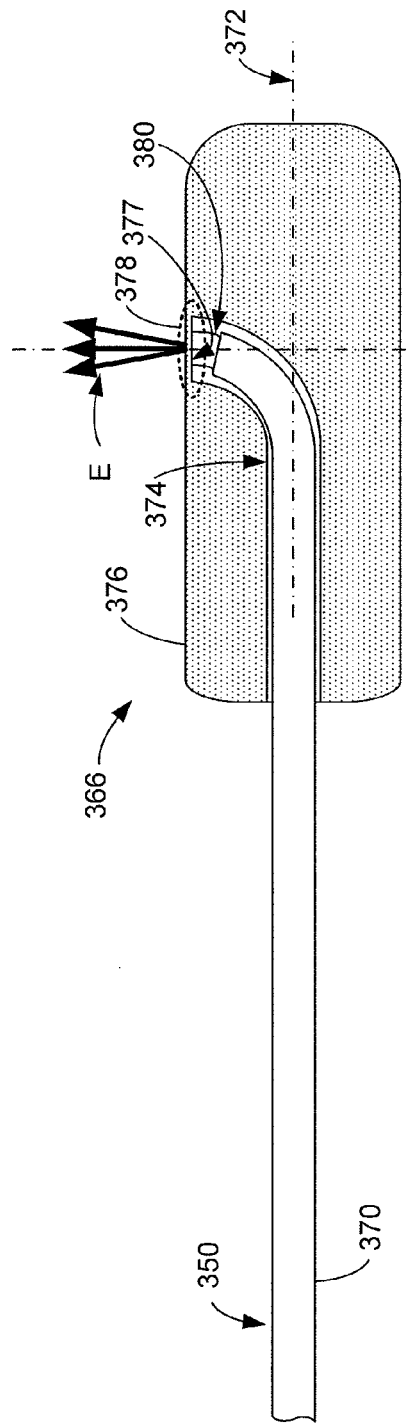

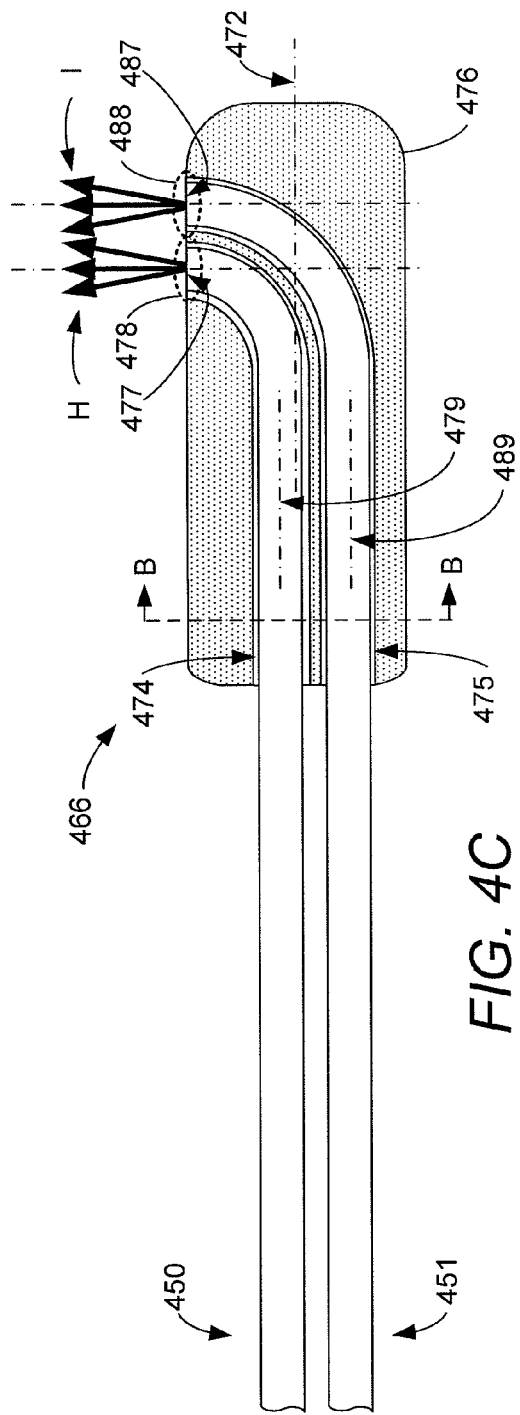
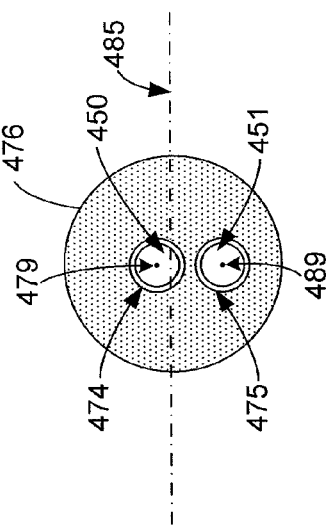
FIG. 4C
FIG. 4D

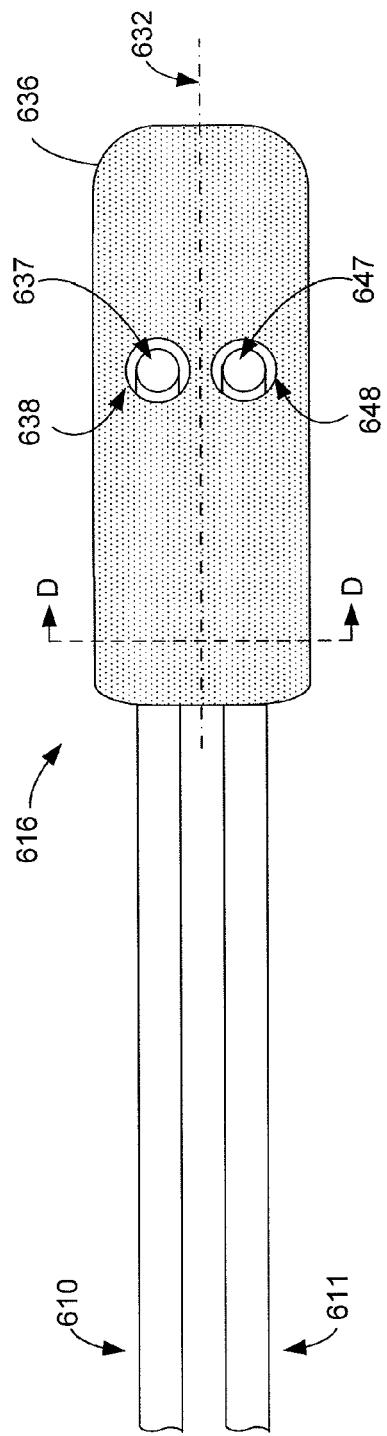
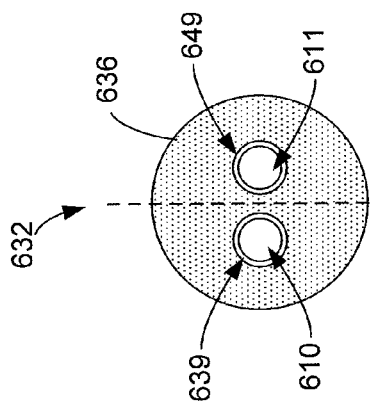
FIG. 6A
FIG. 6B

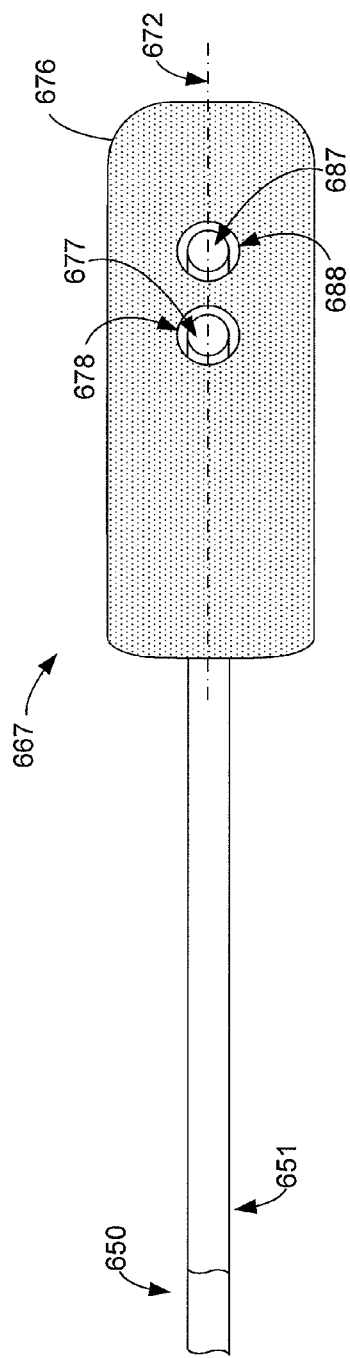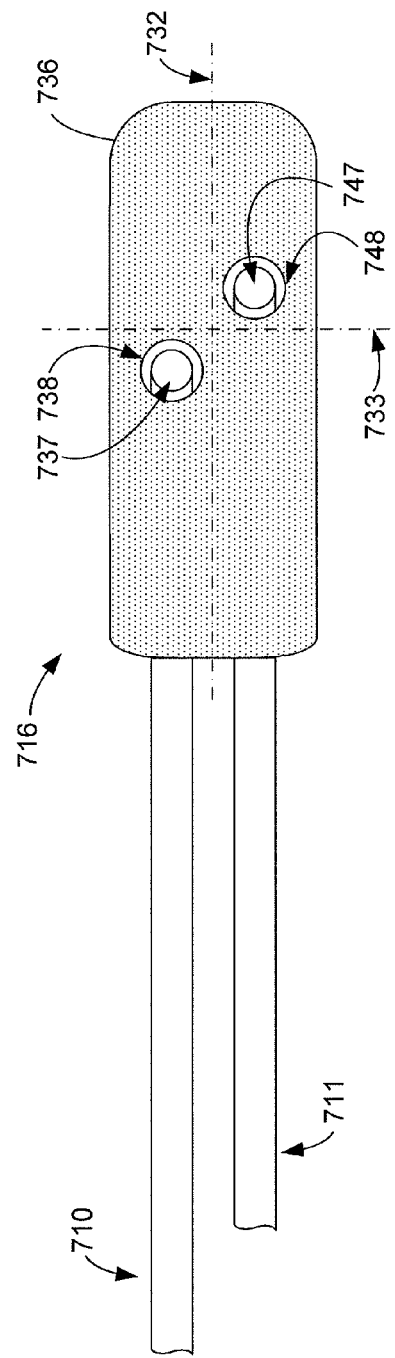
FIG. 6C
FIG. 6D

SIDE-FIRING LASER FIBER WITH INTERNAL BENT FIBER AND RELATED METHODS

RELATED APPLICATION

This application claims priority to and the benefit of U.S. Provisional Application No. 61/054,274, filed on May 19, 2008, entitled "Side-Firing Laser Fiber with Internal Bent Fiber and Related Methods," which is incorporated herein by reference in its entirety.

BACKGROUND

Embodiments relate generally to medical devices and more particularly to side-firing optical fibers and methods for using such devices.

Laser-based surgical procedures using side-firing optical fibers can provide a medical practitioner with more control when applying laser energy to the appropriate treatment area. Passing the distal end portion of the optical fiber through an endoscope during surgery, however, may damage, scratch, degrade, and/or deform the distal end portion of the optical fiber. To protect the optical-fiber end portion, a capillary and/or a metal cap or cannula, usually made of surgical grade stainless steel, can be placed over the optical-fiber end portion. Once the optical-fiber end portion is properly positioned for treatment, the laser energy can be applied to the target area.

During use of the device, a portion of the laser energy can leak from the optical-fiber end portion, reducing the laser energy delivered to the treatment area and/or increasing overheating the metal cap that is typically used to protect the optical fiber. Cooling of the device may be needed to operate at a safe temperature. In some instances, the overheating that can occur from the laser energy leakage can affect the mechanical and/or optical properties of the optical-fiber end portion, the capillary and/or the metal cap. In other instances, the overheating that can occur from the laser energy leakage can be sufficiently severe to damage the optical-fiber end portion, the capillary and/or the metal cap.

Overheating can also occur from the use of reflectors such as metallic reflectors or tips configured to redirect or bend an optical beam about 90 degrees from its original propagation path based on total internal reflection (TIR). Because metallic reflectors do not reflect 100% of the optical beam, the energy associated with the non-reflected portion of the optical beam can be absorbed by the metallic reflector and the metallic reflector can self heat. For TIR-based tips, a portion of the optical beam can leak through and heat up a protective metal cap positioned on a distal end of the tip.

Thus, a need exists for optical fiber end portions that can increase side-fired laser energy, increase device longevity, increase transmission efficiency, reduce overheating, and/or increase patient safety.

SUMMARY

An apparatus according to an embodiment includes a distal end portion of an optical fiber disposed inside a lumen defined along a curved path within a capillary. The distal end surface of the optical fiber can be fixedly disposed and substantially flush with a portion of an outside surface of the capillary that defines a transmissive portion. The distal end portion of the optical fiber and the curved path can be collectively configured to direct laser energy through the transmissive portion in a lateral or side-fired direction that is offset from a longitudinal axis or centerline of the capillary. In some embodiments, more than one optical fiber can be disposed along the curved path. In other embodiments, more than one curved path can be defined within the capillary such that a distal end portion of an optical fiber can be disposed along each of the curved paths.

BRIEF DESCRIPTION OF THE DRAWINGS

FIGS. 1A-1B are schematic representations of an optical fiber side-firing system, according to embodiments.

FIGS. 3A-3E are cross-sectional views of a side-firing optical fiber end portion, according to embodiments.

FIG. 4C is a cross-sectional view of a side-firing optical fiber end portion with multiple optical fibers, according to another embodiment.

FIG. 4D is a cross-sectional view taken along line B-B of FIG. 4C.

FIG. 6A is a top view of a side-firing optical fiber end portion with multiple optical fibers, according to an embodiment.

FIG. 6B is a cross-sectional view taken along line D-D of FIG. 6A.

FIGS. 6C-6E are top views of a side-firing optical fiber end portion with multiple optical fibers, according to embodiments.

DETAILED DESCRIPTION

Figure 2:
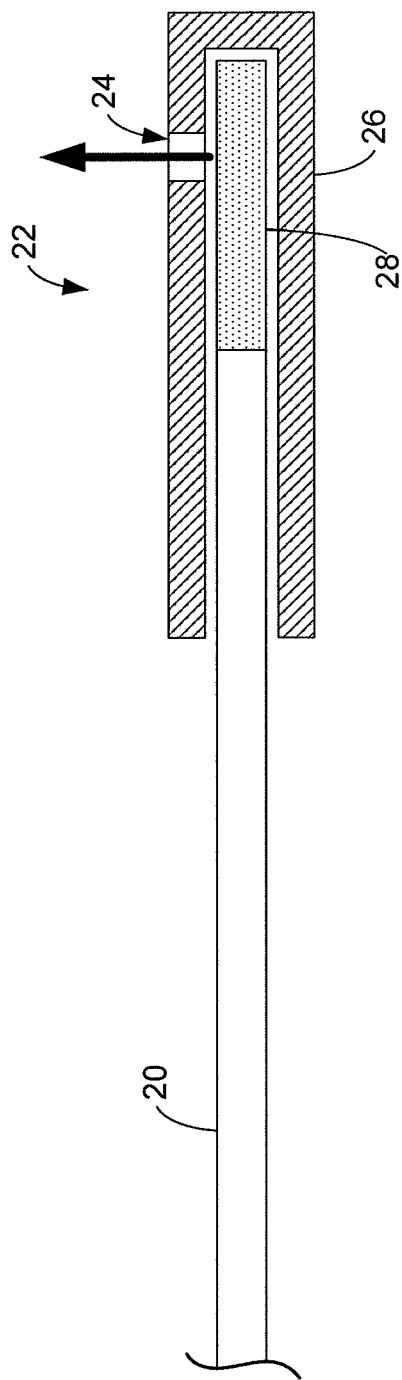
FIG. 2 is a cross-sectional view of a side-firing optical fiber, according to an embodiment.

The devices and methods described herein are generally related to the use of side-firing optical fibers within the body of a patient. For example, the devices and methods can be suitable for use in treating symptoms related to an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists and once the prostate begins to enlarge, it often continues, unless medical treatment is initiated.

Patients who develop symptoms associated with BPH generally need some form of treatment. When the prostate gland is mildly enlarged, research studies indicate that early treatment may not be needed because the symptoms clear up without treatment in as many as one-third of cases. Instead of immediate treatment, regular checkups are recommended. Only if the condition presents a health risk or the symptoms result in major discomfort or inconvenience to the patient is treatment generally recommended. Current forms of treatment include drug treatment, minimally-invasive therapy, and surgical treatment. Drug treatment is not effective in all cases and a number of procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing, for example, side-firing optical fibers and high-power lasers have been used to remove obstructing prostate tissue. In these procedures, a medical practitioner passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization and in most cases the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nm. This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cc (cubic centimeters). Laser-based surgical procedures, such as HoLAP and HoLEP, are becoming more preferable because they produce similar results to those obtained from TURP surgery while having fewer complications and requiring shorter hospital stay, shorter catheterization time, and shorter recovery time.

An optical fiber system as described herein can be used to transmit laser energy from a laser source to a target treatment area within a patient's body. The optical fiber system can include a laser source and an optical fiber. One end of the optical fiber can be coupled to the laser source while the other end of the optical fiber, the distal end portion (e.g., the end with a side-firing portion), can be inserted into the patient's body to provide laser treatment. The distal end portion can include a capillary. In some instances, a metal cap or a low-profile cover can be placed over the capillary. In one embodiment, a distal end portion of an optical fiber can be disposed along a curved path defined within the capillary. The distal end surface of the optical fiber can be fixedly disposed and substantially flush with a transmissive portion of an outside surface of the capillary. The distal end portion of the optical fiber and the curved path can be collectively configured to direct laser energy in a side-firing or laterally-firing direction that is offset from a longitudinal axis or centerline of the capillary. In another embodiment, multiple optical fibers can be disposed along the curved path of the capillary. In yet another embodiment, multiple curved paths can be defined within the capillary such that a distal end portion of an optical fiber can be disposed along each of the curved paths.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., medical practitioner, medical practitioner, nurse, technician, etc.) who would insert the medical device into the patient, with the tip-end (i.e., distal end) of the device inserted inside a patient's body. Thus, for example, the optical fiber end inserted inside a patient's body would be the distal end of the optical fiber, while the optical fiber end outside a patient's body would be the proximal end of the optical fiber.

FIGS. 1A-1B are schematic representations of an optical fiber side-firing system according to an embodiment. As shown in FIG. 1A, an optical fiber side-firing system 10 can include a laser source 11, an optical coupler 12, an optical fiber 14, and an optical-fiber distal end portion 16. The optical fiber side-firing system 10 also includes a suitable catheter or endoscope 15 for inserting the optical-fiber distal end portion 16 into a patient's body. The laser source 11 can include at least one laser that can be used to generate laser energy for surgical procedures. The laser source 11 can include a Ho:YAG laser, for example. The laser source 11 can include at least one of a neodymium-doped:YAG (Nd:YAG) laser, a semiconductor laser diode, or a potassium-titanyl phosphate crystal (KTP) laser, for other examples. In some embodiments, more than one laser can be included in the laser source 11 and more than one laser can be used during a surgical procedure. The laser source 11 can also have a processor that provides timing, wavelength, and/or power control of the laser. For example, the laser source 11 can include mechanisms for laser selection, filtering, temperature compensation, and/or Q-switching operations.

The optical fiber 14 can be coupled to the laser source 11 through the optical coupler 12. The optical coupler 12 can be an SMA connector, for example. The proximal end of the optical fiber 14 can be configured to receive laser energy from the laser source 11 and the distal end of the optical fiber 14 can be configured to output the laser energy through the optical-fiber distal end portion 16. The optical fiber 14 can include, for example, a core, one or more cladding layers about the core, a buffer layer about the cladding, and a jacket. The core can be made of a suitable material for the transmission of laser energy from the laser source 11. In some embodiments, when surgical procedures use wavelengths ranging from about 500 nm to about 2100 nm, the core can be made of silica with a low hydroxyl (OH⁻) ion residual concentration. An example of using low hydroxyl (low-OH) fibers in medical devices is described in U.S. Pat. No. 7,169,140 to Kume, the disclosure of which is incorporated herein by reference in its entirety. The core can be multi-mode and can have a step or graded index profile. The cladding can be a single or a double cladding that can be made of a hard polymer or silica. The buffer can be made of a hard polymer such as Tefzel®, for example. When the optical fiber includes a jacket, the jacket can be made of Tefzel®, for example, or can be made of other polymers.

The endoscope 15 can define one or more lumens. In some embodiments, the endoscope 15 includes a single lumen that can receive therethrough various components such as the optical fiber 14. The endoscope 15 has a proximal end configured to receive the optical-fiber distal end portion 16 and a distal end configured to be inserted into a patient's body for positioning the optical-fiber distal end portion 16 in an appropriate location for a laser-based surgical procedure. For example, to relieve symptoms associated with BPH, the endoscope 15 can be used to place the optical-fiber distal end portion 16 at or near the enlarged portion of the prostate gland. The endoscope 15 includes an elongate portion that can be flexible to allow the elongate portion to be maneuvered within the body. The endoscope 15 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel (not shown) is defined by the endoscope 15 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 15, for example, and coupled to an optical fiber that can be disposed within a lumen of the endoscope 15. Such an embodiment allows a medical practitioner to view the interior of a patient's body through the eyepiece.

The optical-fiber distal end portion 16 can include one or more members, elements, or components that can individually or collectively operate to transmit laser energy in a lateral direction offset from a longitudinal axis or centerline of the distal end of the optical fiber core. In some embodiments, the optical-fiber distal end portion 16 can have a protective metal or ceramic cap or cover. In some instances, it can be desirable to have the cap made of a ceramic material (e.g., alumina) because certain ceramics can offer stable characteristics at high-temperatures and/or have a high reflectance value at the laser operating wavelength. In other embodiments, the optical-fiber distal end portion 16 can have a protective low-profile coating or a low-profile slideable sleeve or tubing than can be retracted to expose the optical-fiber distal end portion 16 to a treatment area during a surgical procedure.

In FIG. 1B, an optical fiber side-firing system 18 is shown that can include the laser source 13, more than one optical couplers 12, an optical fiber bundle 17, and an optical-fiber distal end portion 19. The optical fiber side-firing system 13 can also include the catheter or endoscope 15 for inserting the optical-fiber distal end portion 19 into a patient's body. The optical fiber bundle 17 can include multiple optical fibers. In one embodiment, laser energy from a single laser in the laser source 13 can be transmitted through one or more of the optical fibers in the optical fiber bundle 17. In another embodiment, laser energy from multiple lasers in the laser source 13 can be transmitted through one or more of the optical fibers in the optical fiber bundle 17. The optical-fiber distal end portion 19 can include one or more members, elements, or components that can operate to transmit laser energy in a lateral direction offset from the longitudinal axis or centerline of the distal end of the optical fiber core. The optical-fiber distal end portion 19 can include a protective metal or ceramic cap or cover and/or a low-profile coating such as a polymer coating, for example.

FIG. 2 is a cross-sectional view of an optical-fiber distal end portion, according to an embodiment. As shown in FIG. 2, a optical-fiber distal end portion 22 can include an inner portion 28 and surrounded by an outer portion 26. The outer portion 26 can include a high-profile member such as, for example, a metal cover or cap. The outer portion 26 can provide protection to the optical-fiber distal end portion 22. In some embodiments, the outer portion 26 can include a low-profile coating or a low-profile sleeve.

The outer portion 26 can include a window or transmissive portion 24 through which laterally-redirected or side-fired laser energy can be transmitted for surgical treatment. For example, when the outer portion 26 is made of an opaque material, a window can be defined after removing at least a portion of the opaque material. In another example, when the outer portion 26 is made of an optically-transmissive material, laser energy can be transmitted or sent through the outer portion 26. In some embodiments, the optically-transmissive material can be treated thermally, optically, mechanically, and/or chemically to improve its structural and/or optical characteristics such that laser energy can be delivered more effectively to the target area. For example, the optically-transmissive material can be thermally treated during manufacturing using a $CO_2$ laser.

The inner portion 28 can include one or more members, components, and/or devices to redirect laser energy. For example, the inner portion 28 can include a capillary or capillary tube. The capillary can be made of, for example, at least one of silica, sapphire, and/or other like materials. In one embodiment, the inner portion 28 can include a distal end portion of optical fiber 20 disposed within a capillary. As described below in more detail, the inner portion 28 can also include components, members and/or devices that can be used to redirect laser energy to provide side-firing operations.

Figure 3C:
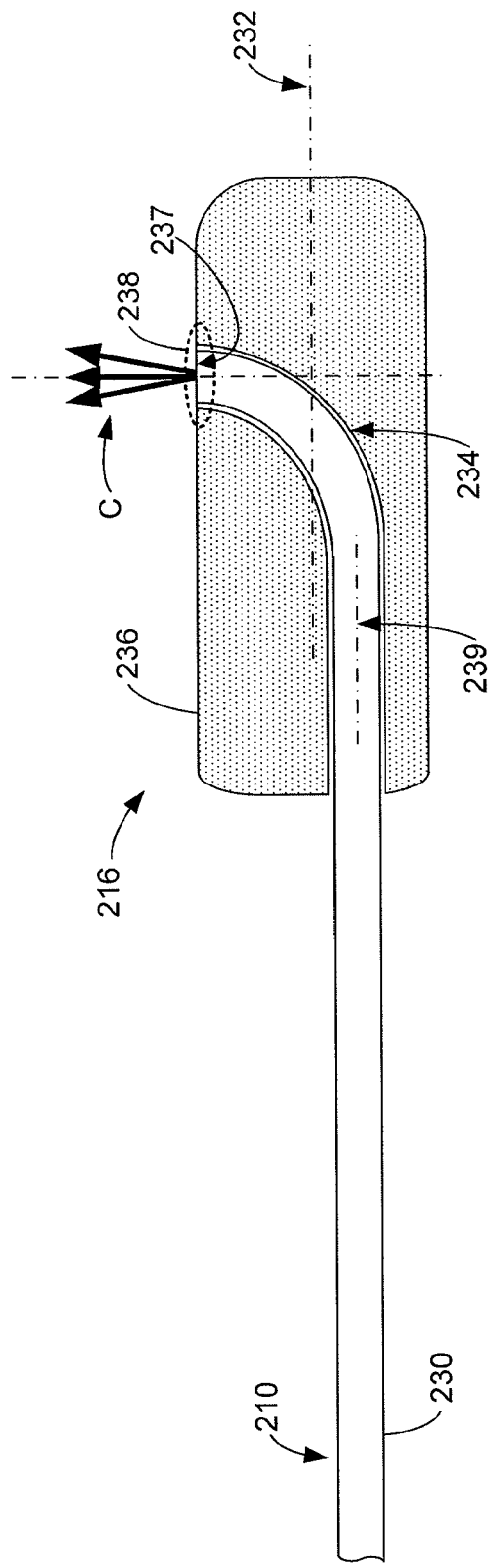

FIGS. 3A-3E are cross-sectional views of a side-firing optical fiber end portion, according to embodiments. As shown in FIG. 3A, a side-firing optical fiber end portion 116 can include a capillary 136 having a lumen or curved path 134 defined by the interior of the capillary 136. A distal end portion of an optical fiber 110 can be disposed along the lumen 134. The optical fiber 110 has a buffer layer 130, a cladding layer (not shown), and an optical-fiber-core (not shown). In some embodiments, a proximal end portion of the capillary 136 can be coupled to the buffer layer 130 of the side-firing optical fiber 110.

A terminating or distal end surface 137 of the optical fiber 110 can be fixedly disposed and substantially flush or even with a portion of an outer surface of the capillary 136 that defines a transmissive portion 138 and located at a distal end of the lumen 134. In this regard, the distal end surface 137 can be cleaved and/or polished such that it can be fixedly disposed and substantially flush with the transmissive portion 138. The transmissive portion 138 can be, for example, an opening or a hole defined by the outer surface of the capillary 136 through which a laser energy A can be transmitted. The transmissive portion 138 can be offset from a longitudinal axis or centerline 132 of the distal end portion of the capillary 136 such that the laser energy A can be transmitted in a side-fired or laterally-fired direction.

The distal end portion of the optical fiber 110 disposed within the capillary 136 can substantially conform to the curved surfaces along the lumen 134. In some embodiments, a thermal process, for example, can be used to appropriately bend the distal end portion of the optical fiber 110 prior to being disposed or inserted within the capillary 136 through a proximal end of the curved path 314. The curved surfaces along the lumen 134 can be determined, defined, and/or designed based on the location of the transmissive portion 138 and on the size, shape, and/or properties of the capillary 136 and/or of the optical fiber 110. For example, mechanical properties of the capillary 136 and/or of the optical fiber 110 may be considered when determining the size and/or shape of the lumen 134. The curved surfaces along the lumen 134 can be configured such that laser energy can be directed in a lateral or side-fired direction for medical treatment.

FIG. 3B is a cross-sectional view of a side-firing optical fiber end portion 166 that includes a capillary 176. The capillary 176 defines a lumen 174 within which a distal end portion of an optical fiber 150 can be disposed. In some embodiments, a proximal end portion of the capillary 176 can be coupled to a buffer layer 170 of the optical fiber 150. A distal end surface 177 of the optical fiber 150 can be fixedly disposed and substantially flush with a portion of an outer surface of the capillary 176 that defines a transmissive portion 178. The transmissive portion 178 can include an optically-transmissive thin layer of the outer surface of the capillary 176. In this regard, the transmissive portion 178 can be used to limit the distal end portion of the optical fiber 150 from sliding in a distal direction beyond the location of the transmissive portion 178. The transmissive portion 178 can be offset from a longitudinal axis or centerline 172 of the distal end portion of the capillary 176 such that a laser energy B can be transmitted in a side-fired or laterally-fired direction.

FIG. 3C is a cross-sectional view of a side-firing optical fiber end portion 216. As shown in FIG. 3C, a capillary 236 can define a lumen 234 within which a distal end portion of an optical fiber 210 can be disposed. A distal end surface 237 of the optical fiber 210 can be fixedly disposed and substantially flush with a portion of an outer surface of the capillary 236 that defines a transmissive portion 238. The transmissive portion 238 can be offset from a longitudinal axis or centerline 232 of the distal end portion of the capillary 236 such that a laser energy C can be transmitted in a side-fired direction.

In some embodiments, the radius of curvature of curved surfaces along the length of the lumen 234 can be larger than those of the curved surfaces along the curved paths shown in FIGS. 3A and 3B. For example, a centerline 239 along the non-curved portion of the optical fiber 210 that is disposed within the capillary 236 can be spaced or disposed offset from the longitudinal axis or centerline 232 of the capillary 236 in a direction opposite the side-firing direction. This offset can produce curved surfaces along the length of the lumen 234 that have a larger radius of curvature than as shown in FIGS. 3A and 3B. A larger radius of curvature along the length of the curved surfaces of the lumen 234 may, in some instances, facilitate the inserting, curving, and/or positioning of the distal end portion of the optical fiber 210 within the capillary 236. A smaller capillary size or profile, however, can result in those instances when the curved surfaces along the length of the lumen have a smaller radius of curvature.

As shown in FIG. 3D, a side-firing optical fiber end portion 316 can include a capillary 336. The capillary 336 can define a lumen 334 such that a distal end portion of an optical fiber 310 can be disposed along the lumen 334. The optical fiber 310 has a buffer layer 330, a cladding layer (not shown), and an optical-fiber-core end portion 340. The distal end of the optical-fiber-core end portion 340 can be offset from a distal end of the buffer layer 330 and from a distal end of the cladding layer. A distal end surface 337 of the optical-fiber-core end portion 340 can be fixedly disposed and substantially flush with a portion of an outer surface of the capillary 336 that defines a transmissive portion 338. The transmissive portion 338 can be offset from a longitudinal axis or centerline 332 of the distal end portion of the capillary 336 such that a laser energy D can be transmitted in a side-fired direction.

FIG. 3E is a cross-sectional view of a side-firing optical fiber end portion 366 with a capillary 376 that defines a curved path 374. A distal end portion of a side-firing optical fiber 350 can be disposed along the curved path 374. The side-firing optical fiber 350 has a buffer layer 370, a cladding layer (not shown), and an optical-fiber-core end portion 380. The distal end of the optical-fiber-core end portion 380 can be offset from a distal end of the buffer layer 370 and from a distal end of the cladding layer.

A distal end surface 377 of the optical-fiber-core end portion 380 can be fixedly disposed and substantially flush with a portion of an outer surface of the capillary 376 that defines a transmissive portion 378. The transmissive portion 378 can include an optically-transmissive thin layer of the outer surface of the capillary 376 that can limit the distal end of the optical-fiber-core end portion 380 from sliding in a distal direction beyond the location of the transmissive portion 378. The transmissive portion 378 can be offset from a longitudinal axis or centerline 372 of the distal end portion of the capillary 376 such that a laser energy E can be transmitted in a side-fired direction.

Figure 4A:
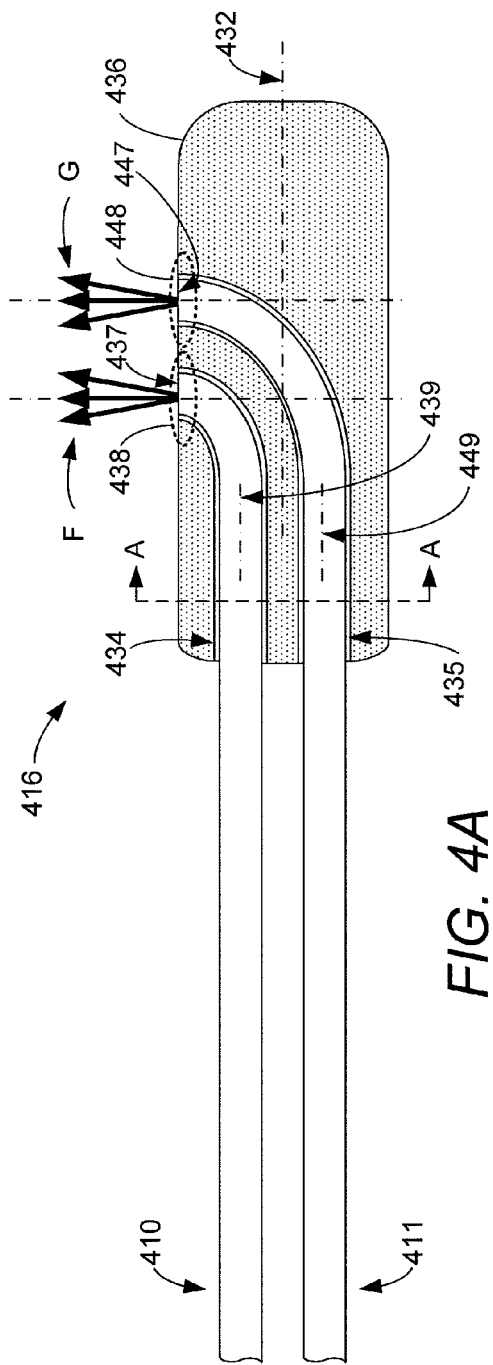
FIG. 4A is a cross-sectional view of a side-firing optical fiber end portion with multiple optical fibers, according to an embodiment.

FIG. 4A is a cross-sectional view of a side-firing optical fiber end portion with multiple optical fibers, according to an embodiment. A side-firing optical fiber end portion 416 can include a capillary 436 having a first lumen 434 and a second lumen 435. A distal end portion of an optical fiber 410 can be disposed along the first lumen 434. Similarly, a distal end portion of an optical fiber 411 can be disposed along the second lumen 435. By having more than one optical fiber, the side-firing optical fiber end portion 416 can provide a medical practitioner with more flexibility regarding the location or area of laser-based treatment, the amount of laser energy that can be applied, the wavelengths of laser energy, and/or the sources of laser energy that can be used during a surgical procedure. Having more than one optical fiber disposed within the capillary, however, may require a larger capillary size or profile.

A first distal end surface 437 of the optical fiber 410 can be fixedly disposed and substantially flush with a portion of an outer surface of the capillary 436 that defines a first transmissive portion 438. A second distal end surface 447 of the optical fiber 411 can be fixedly disposed and substantially flush with a portion of the outer surface of the capillary 436 that defines a second transmissive portion 448. The transmissive portions 438 and 448 can be, for example, an opening or a hole defined by the outer surface of the capillary 436 through which laser energies F and G can be transmitted, respectively. The transmissive portions 438 and 448 can be offset from a longitudinal axis or centerline 432 of a distal end portion of the capillary 436 such that the laser energies F and G can be transmitted in a side-fired direction.

The radius of curvature of the curved surfaces along the length of the second lumen 435 can be different than the those of the curved surfaces along the length of the first lumen 434. For example, a centerline 439 along the non-curved distal end portion of the optical fiber 410 can be spaced offset from the longitudinal axis or centerline 432 of the capillary 436. In another example, a centerline 449 along the non-curved distal end portion of the optical fiber 411 can be spaced offset from the longitudinal axis or centerline 432 of the capillary 436. These offsets can produce a radius of curvature of the curved surfaces along the length of the second lumen 435 that are larger than those of the curved surfaces along the length of the first lumen 434. The size or profile of the capillary 436 may depend, at least partially, on the radius of curvature of the curved surfaces along the length of the first and second lumens 434 and 435.

Figure 4B:
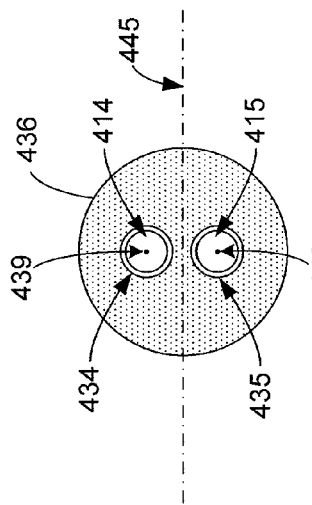
FIG. 4B is a cross-sectional view taken along line A-A of FIG. 4A.

FIG. 4B is a cross-sectional view taken along line A-A of FIG. 4A where a proximal end portion of the first lumen 434 is shown spaced offset from a plane 445. The plane 445 can include the longitudinal axis or centerline 432. Moreover, a proximal end portion of the second lumen 435 is shown spaced offset from the plane 445. In this regard, the centerline 439 and the centerline 449 are approximately equally offset from the plane 445. Also shown in FIG. 4B are the optical fiber 410 disposed within the first lumen 434 and the optical fiber 411 disposed within the second lumen 435.

FIG. 4C is a cross-sectional view of a side-firing optical fiber end portion with multiple optical fibers, according to an embodiment. A side-firing optical fiber end portion 466 can include a capillary 476 having a first lumen 474 and a second lumen 475. A distal end portion of an optical fiber 450 and of an optical fiber 451 can be disposed along the first lumen 474 and along the second lumen 475, respectively. A first distal end surface 477 and a second distal end surface 487 can be fixedly disposed and substantially flush with portions of an outer surface of the capillary 476 that define a first transmissive portion 478 and a second transmissive portion 488, respectively. The transmissive portions 478 and 488 can each be, for example, an opening or a hole defined by the outer surface of the capillary 476 through which respective laser energies H and I can be transmitted in a side-fired direction.

The radius of curvature of the surfaces along the length of the first lumen 474 and along the length of the second lumen 475 can be different than as shown along the length of the first lumen 434 and along the length of the second lumen 435 in FIG. 4A. For example, a centerline 479 along the non-curved distal end portion of the optical fiber 450 can be spaced offset from a longitudinal axis or centerline 472 of the capillary 476. In another example, a centerline 489 along the non-curved distal end portion of the optical fiber 451 can be spaced offset from the longitudinal axis or centerline 472 of the capillary 476. These offsets can produce radius of curvature of the surfaces along the length of the first lumen 474 and along the length of the second lumen 475 that are larger than those shown in FIG. 4A. As described above, a larger radius of curvature of surfaces along a lumen may, in some instances, facilitate the inserting, curving, and/or positioning of the distal end portion of the optical fiber within the capillary. A smaller capillary size or profile, however, can result when a smaller radius of curvature is used for the surfaces along the length of the lumen or curved path.

FIG. 4D is a cross-sectional view taken along line B-B of FIG. 4C where a proximal end portion of the first lumen 474 is shown spaced offset from a plane 485 in one direction. The plane 485 can include the longitudinal axis or centerline 472. A proximal end portion of the second lumen 475 is shown spaced offset from the plane 485 in the direction opposite the direction in which the first lumen 474 is offset. In this regard, the centerline 479 is offset from the plane 485 less than that of the centerline 489. Also shown in FIG. 4D are the optical fibers 450 and 451 disposed within the first lumen 474 and within the second lumen 475, respectively.

Figure 5A:
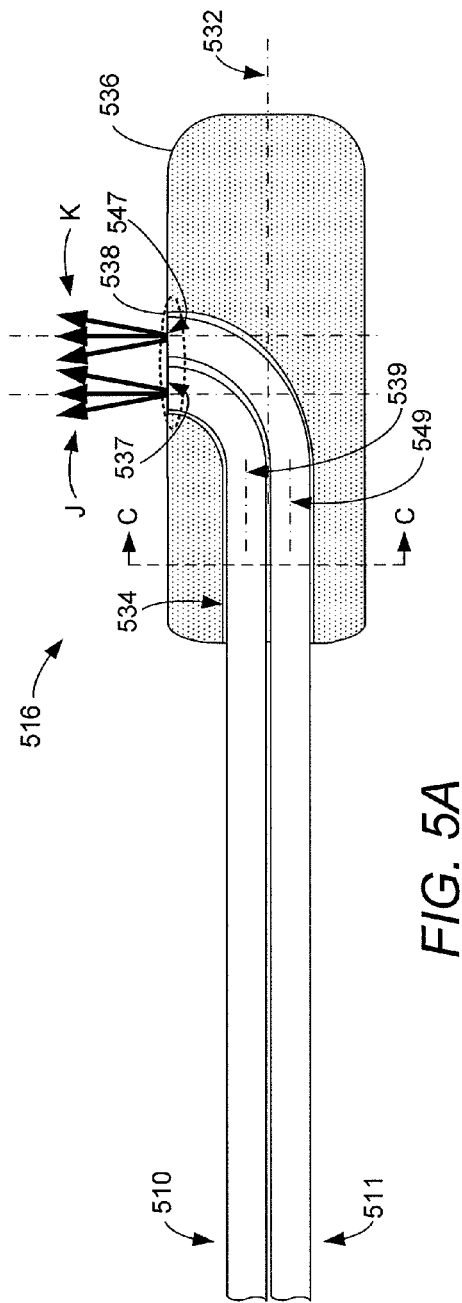
FIG. 5A is a cross-sectional view of a side-firing optical fiber end portion with multiple optical fibers, according to another embodiment.

FIG. 5A is a cross-sectional view of a side-firing optical fiber end portion with multiple optical fibers, according to another embodiment. A side-firing optical fiber end portion 516 can include a capillary 536 having a lumen 534. A distal end portion of an optical fiber 510 and a distal end portion of an optical fiber 511 can be disposed along the lumen 534. A first distal end surface 537 of the optical fiber 510 and a second distal end surface 547 of the optical fiber 511 can be fixedly disposed and substantially flush a portion of an outer surface of the capillary 536 that defines a transmissive portion 538. The transmissive portion 538 can be, for example, an opening or a hole defined by the outer surface of the capillary 536 through which laser energies J and K can be transmitted, respectively. The transmissive portion 538 can be offset from a longitudinal axis or centerline 532 of a distal end portion of the capillary 536 such that the laser energies J and K can be transmitted in a side-fired direction.

A centerline 539 along the non-curved distal end portion of the optical fiber 510 is spaced offset from the longitudinal axis or centerline 532 in one direction. Similarly, a centerline 549 along the non-curved distal end portion of the optical fiber 511 is spaced offset from the longitudinal axis or centerline 532 in a direction opposite of the direction in which the centerline 539 is offset. These offsets can produce radius of curvature along the length of the curved portion of the optical fiber 511 that are larger than those along the length of the curved portion of the optical fiber 510.

Figure 5C:
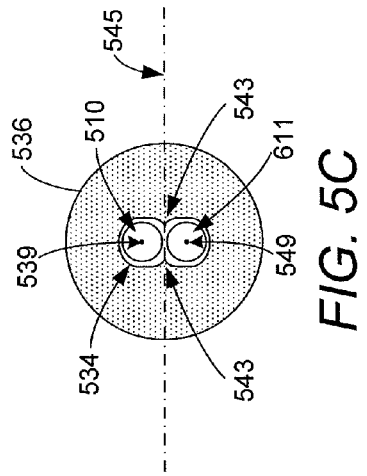
FIG. 5C is a cross-sectional view taken along line C-C of FIG. 5A, according to another embodiment.
Figure 5B:
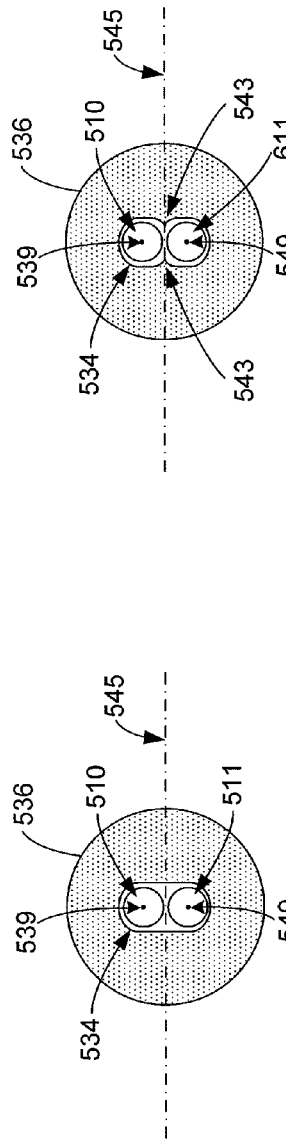
FIG. 5B is a cross-sectional view taken along line C-C of FIG. 5A, according to an embodiment.

FIG. 5B is a cross-sectional view taken along line C-C of FIG. 5A. In the embodiment shown in FIG. 5B, the optical fiber 510 and the optical fiber 511 are disposed within a proximal end portion of the lumen 534. The centerline 539 and the centerline 549 are approximately equally offset from a plane 545 that can include the longitudinal axis or centerline 532. FIG. 5C is a cross-sectional view taken along line C-C of FIG. 5A which shows another embodiment in which the lumen 534 has ridges 543 to facilitate the positioning of the optical fibers 510 and 511 within the lumen 534. Although not shown in FIG. 5C, the ridges 543 can be disposed along the length of the lumen 534. In other embodiments, however, the ridges 543 are not continuous along the length of the lumen 534. In addition, other members, components, and/or elements can be used and/or can be defined within the capillary 536 to hold, maintain, and/or position the optical fibers 510 and 511 within the lumen 534.

FIG. 6A is a top view of a side-firing optical fiber end portion with multiple optical fibers, according to an embodiment. A side-firing optical fiber end portion 616 can include a capillary 636 within which a distal end portion of an optical fiber 610 and a distal end portion of an optical fiber 611 can be disposed. A first distal end surface 637 of the optical fiber 610 can be fixedly disposed and substantially flush with a portion of an outer surface of the capillary 636 that defines a transmissive portion 638. A second distal end surface 647 of the optical fiber 611 can be fixedly disposed and substantially flush with a portion of the outer surface of the capillary 636 that defines a transmissive portion 648. The transmissive portion 638 can be defined on the outer surface of the capillary 636 offset from a plane 632 in one direction and the transmissive portion 648 can be defined on the outer surface of the capillary 636 offset from the plane 632 in a direction opposite of the direction for the transmission portion 638.

FIG. 6B is a cross-sectional view taken along line D-D of FIG. 6A where a proximal end portion of the a first lumen 639 and of a second lumen 649 are shown. The first lumen 639 can be disposed offset from the plane 632 in one direction and the second lumen 649 can be disposed offset from the plane 632 in a direction opposite of the direction of the first lumen 639.

Also shown in FIG. 6B are the optical fiber 610 disposed within the first lumen 639 and the optical fiber 611 disposed within the second lumen 649.

In another embodiment, as shown in FIG. 6C, a side-firing optical fiber end portion 667 can include a capillary 676 within which a distal end portion of an optical fiber 650 and a distal end portion of an optical fiber 651 can be disposed. A first distal end surface 677 of the optical fiber 651 can be fixedly disposed and substantially flush with an outer surface of the capillary 676 that defines a transmissive portion 678. A second distal end surface 687 of the side-firing optical fiber 650 can be fixedly disposed and substantially flush with an outer surface of the capillary 676 that defines a transmissive portion 688.

In another embodiment, as shown in FIG. 6D, a side-firing optical fiber end portion 716 can include a capillary 736 within which a distal end portion of an optical fiber 710 and a distal end portion of an optical fiber 711 can be disposed. A first distal end surface 737 of the optical fiber 710 can be fixedly disposed and substantially flush with an outer surface of the capillary 736 that defines a transmissive portion 738. A second distal end surface 747 of the optical fiber 711 can be fixedly disposed and substantially flush an outer surface of the capillary 736 that defines a transmissive portion 748. The transmissive portion 738 can be defined offset from a plane 732 in one direction and the transmissive portion 748 can be defined offset from the plane 732 in a direction opposite of the direction of the transmissive portion 738. Moreover, the transmissive portions 738 and 748 can be offset from each other with respect to a plane 733.

Figure 6E:
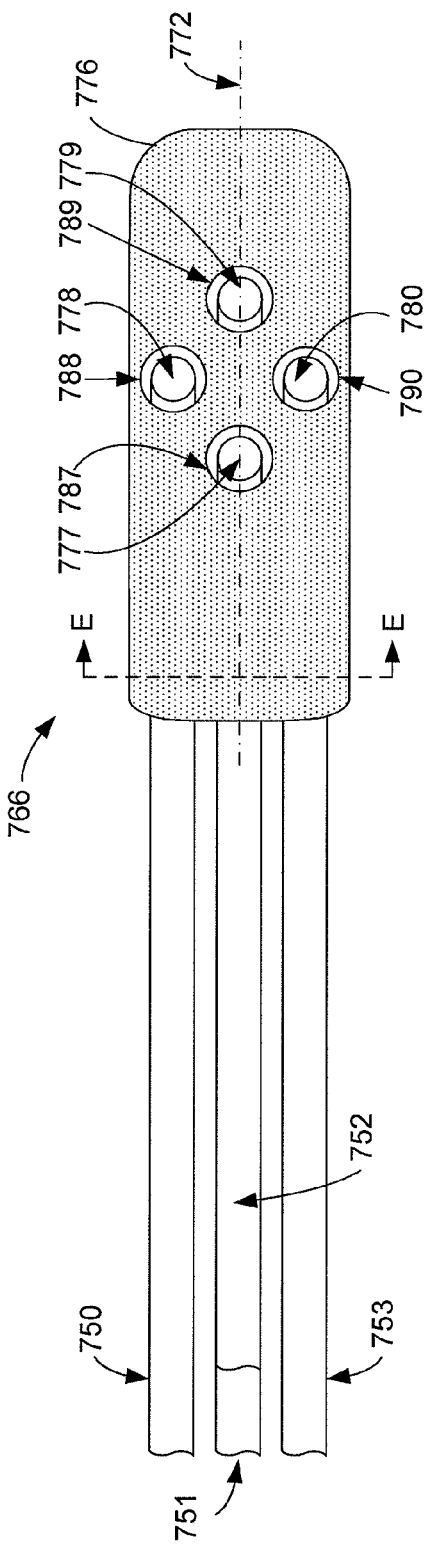
Figure 6F:
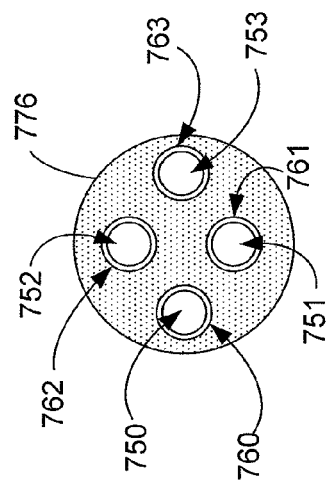
FIG. 6F is a cross-sectional view taken along line E-E of FIG. 6E.

FIG. 6E is a top view of a side-firing optical fiber end portion with multiple optical fibers, according to another embodiment. A side-firing optical fiber end portion 766 can include a capillary 776 within which a distal end portion of optical fibers 750, 751, 752, and 753 can be disposed. Distal end surfaces 777, 778, 779, and 780 corresponding to the optical fibers 752, 750, 751, and 753 can be fixedly disposed and substantially flush with portions of an outer surface of the capillary 776 that define transmissive portions 787, 788, 789, and 790, respectively. The transmissive portions 787 and 789 can be defined about a plane 772. The transmissive portion 788 can be defined offset from the plane 772 in one direction and the transmissive portion 790 can be defined offset from the plane 772 in a direction opposite of the direction of the transmissive portion 788. FIG. 6F is a cross-sectional view taken along line E-E of FIG. 6E. As shown in FIG. 6F, the optical fibers 750, 751, 752, and 753 can be disposed within the lumens 760, 761, 762, and 763, respectively.

Figure 7:
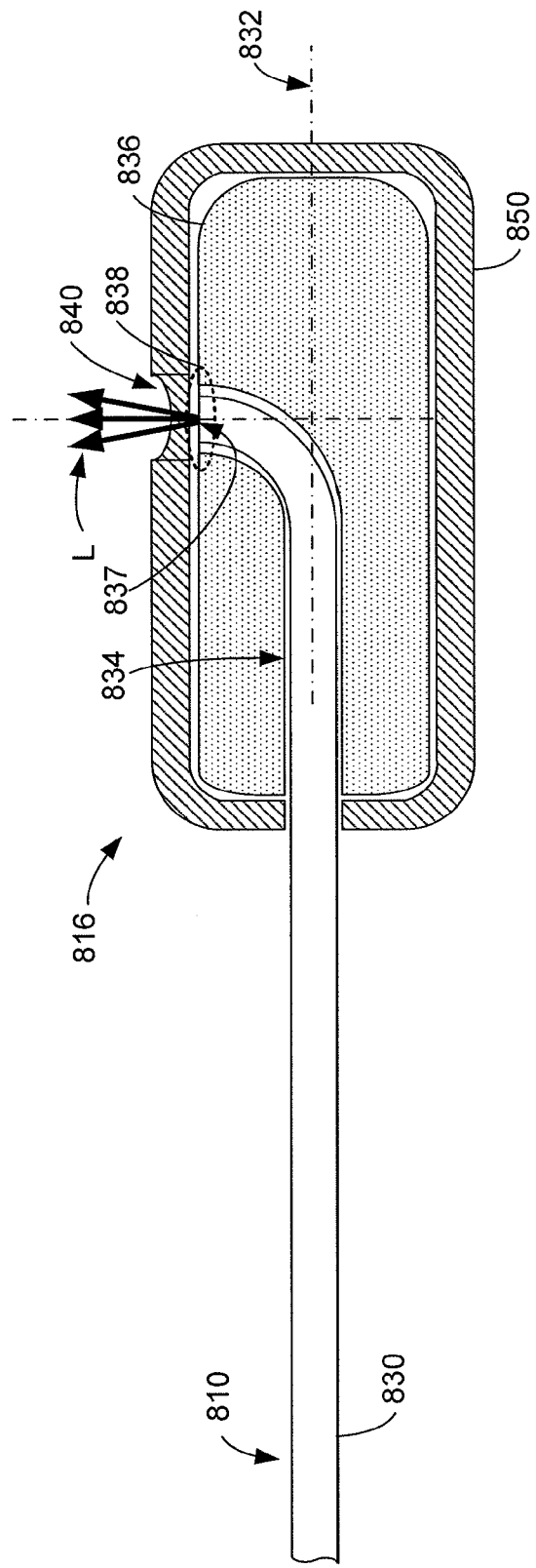
FIG. 7 is a cross-sectional view of a side-firing optical fiber end portion with a protective cap, according to an embodiment.

FIG. 7 is a cross-sectional view of a side-firing optical fiber end portion with a protective cap, according to an embodiment. A side-firing optical fiber end portion 816 can include a capillary 836 having a lumen 834 defined by the interior of the capillary 836. A distal end portion of an optical fiber 810 can be disposed along the lumen 834. The optical fiber 810 may include a buffer layer 830, a cladding layer (not shown), and an optical-fiber-core (not shown). A distal end surface 837 of the optical fiber 810 can be fixedly disposed and substantially flush with a portion of an outer surface of the capillary 836 that defines a transmissive portion 838. The transmissive portion 838 can be located at a distal end of the lumen 834 and can be offset from a longitudinal axis or centerline 832 of the distal end portion of the capillary 836 such that the laser energy L can be transmitted in a side-fired direction.

The capillary 836 can be disposed within an outer member 850 that is configured to be disposed within a patient's body. The outer member 850 can be made of an optically-opaque material, such as a metal cap and/or a polymer-based coating, for example. A transmissive portion 840, such as a hole or opening, for example, can be defined on the outer member 850 in a location that is offset from the longitudinal axis or centerline 832. The transmissive portion 840 can be at least partially aligned with the transmissive portion 838 of the capillary 836 such that the laser energy L can be transmitted through the transmissive portion 840 during a side-fired surgical procedure.

Figure 8:
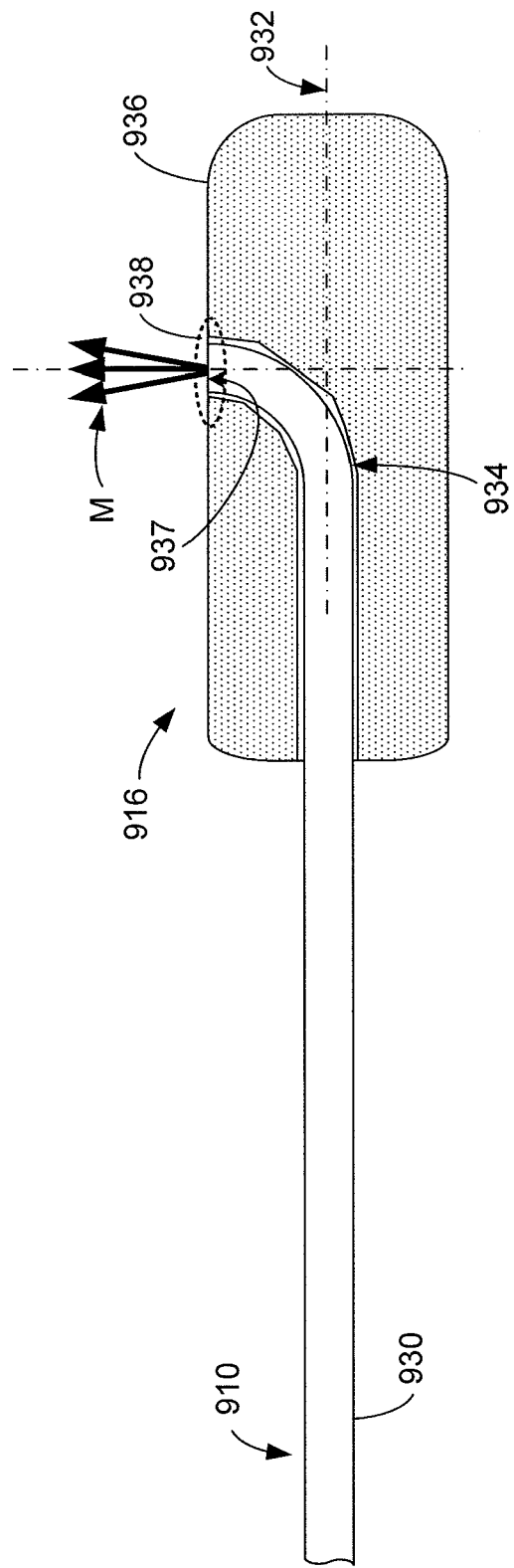
FIG. 8 is a cross-sectional view of a side-firing optical fiber end portion with a segmented curved path within the capillary, according to an embodiment.

FIG. 8 is a cross-sectional view of a side-firing optical fiber end portion with a segmented curved path within the capillary, according to an embodiment. A side-firing optical fiber end portion 916 is shown having a capillary 936 with a lumen 934 defined by the interior of the capillary 936. Laser energy M can be transmitted in a side-fired direction from a distal end surface 937 of an optical fiber 910 that can be fixedly disposed and substantially flush with a portion of an outer surface of the capillary 936 that defines a transmissive portion 938. The optical fiber 910 may include a buffer layer 930, a cladding layer (not shown), and an optical-fiber-core (not shown). The lumen 934 is shown to include multiple linear segments defined within the capillary 936. In other embodiments, the lumen 934 can include multiple linear and/or non-linear or curved segments defined within the capillary 936. The number, shape, and/or size of the segments may depend on the location of the transmissive portion 938, the material properties of the capillary 936, and/or on the manufacturing process used to define the lumen 934. The segments of the curved path 934 collectively provide for transmission of the laser energy M in a side-fired direction.

In the embodiments described in FIGS. 4B, 4D, 5B, 5C, 6B, and 6F, the capillaries and/or the curved paths have been shown as having substantially circular cross sections, however, other embodiments can include different cross-sectional shapes and/or sizes from those of the different embodiments described. Moreover, in some embodiments with multiple optical fibers, the location, number, and/or shape of the transmissive portions defined by the outer surface of the capillary can vary from those of the different embodiments described.

Figure 9:
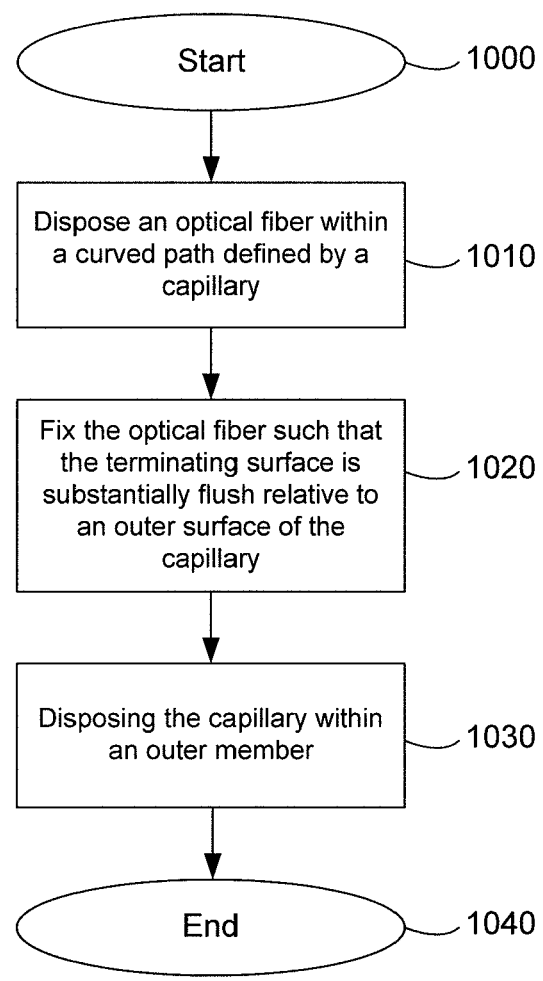
FIGS. 9-10 are flow charts illustrating a method according to an embodiment.

FIG. 9 is a flow chart illustrating a method for manufacturing a side-firing optical fiber system, according to an embodiment. At 1010, after start 1000, a distal end portion of an optical fiber can be disposed along a lumen defined by the interior of a capillary. In some embodiments, more than one optical fiber can be disposed within the lumen. In other embodiments, the capillary can have more than one lumen defined within such that a distal end portion of an optical fiber can be disposed within each of the lumens. At 1020, a terminating or distal end surface of the optical fiber can be fixedly disposed and substantially flush with a portion of an outer surface of the capillary that defines a transmissive portion, such as a hole or opening, for example. The transmissive portion can be defined offset a longitudinal axis or centerline of a distal end of the capillary. In some embodiments, where the capillary is configured to have more than one optical fiber, more than one transmissive portion can be defined by the outer surface of the capillary. At 1030, the capillary can be disposed within an outer member having a transmissive portion that is at least partially aligned with the transmissive portion of the capillary. After 1030, the method can proceed to end 1040.

Figure 10:
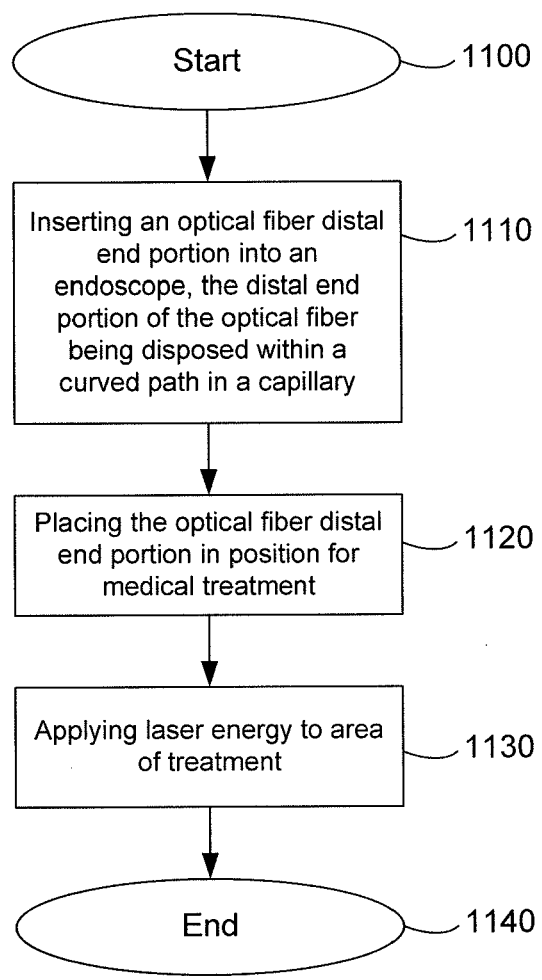

FIG. 10 is a flow chart illustrating a method of using an optical fiber system, according to another embodiment. At 1110, after start 1100, an optical-fiber distal end portion can be inserted within an inner portion or lumen of an elongated member such as, for example, an endoscope. The optical-fiber distal end portion can be side-firing. The optical-fiber distal end portion can be disposed along a lumen defined by the interior of a capillary. A distal end surface of the optical fiber can be fixedly disposed and substantially flush with a transmissive portion defined by an outer surface of the capillary.

At 1120, the endoscope can be at least partially placed in a position for laser-based treatment by inserting the endoscope into the patient's body during a surgical procedure. In some BPH procedures, the medical practitioner can reach the prostate by inserting the instrument through the urethra. In other instances, when a transurethral procedure may not be used, a percutaneous approach may be used to insert the side-firing laser for treatment. Once inserted into the patient's body, the endoscope can be used to place or position the optical-fiber distal end portion at or near the area of treatment. At 1130, for side-fired surgical procedures, laser energy from a laser source can be applied to a treatment area by being transmitted through the optical fiber such that the laser energy is side-fired or laterally redirected at the optical-fiber distal end portion. After 1130, the method can proceed to end 1140.

While various embodiments have been described above, it should be understood that they have been presented by way of example only, and not limitation. For example, the optical fiber side-firing systems described herein can include various combinations and/or sub-combinations of the components and/or features of the different embodiments described. Although described with reference to use for treatment of symptoms related to BPH, it should be understood that the optical fiber systems and/or the optical fibers described herein, as well as the methods of using the optical fiber systems and/or the optical fibers described herein, can be used in the treatment of other conditions.

Embodiments of a side-firing optical fiber can also be provided without the optical fiber side-firing system described herein. For example, a side-firing optical fiber can be configured to be used with other laser sources, endoscopes, etc., not specifically described herein. A side-firing optical fiber can have a variety of different shapes and sizes than as illustrated and described herein. A side-firing optical fiber can also include other features and/or components such as, for example, lenses and/or filters.

What is claimed is:

1. An apparatus, comprising:
a member having an outer surface that includes a transmissive portion, the transmissive portion being offset from a centerline of the member; and
an optical fiber having a proximal end portion and a distal end portion, the proximal end portion of the optical fiber configured to be coupled to a laser source, at least a portion of the distal end portion of the optical fiber being fixedly disposed within the member along a curved path, a terminating surface of the distal end portion of the optical fiber being flush with a portion of the outer surface of the member that defines the transmissive portion; and
an outer member, the member being disposed within the outer member, the outer member having a transmissive portion and a blunt distal end, the transmissive portion of the outer member being at least partially aligned with the transmissive portion of the member.

2. The apparatus of claim 1, wherein the transmissive portion of the outer surface of the member includes an opening.

3. The apparatus of claim 1, wherein the curved path includes a plurality of segments.

4. The apparatus of claim 1, wherein the optical fiber includes a core, a cladding disposed about the core, and a buffer disposed about the cladding, a distal end of the core being offset from a distal end of the cladding and a distal end of the buffer.

5. The apparatus of claim 1, wherein the optical fiber includes a core, a terminating surface of a distal end portion of the core being flush with the portion of the outer surface of the member that defines the transmissive portion.

6. The apparatus of claim 1, wherein the optical fiber is a first optical fiber, the apparatus further comprising a second optical fiber, a distal end portion of the second optical fiber being disposed within the member along the curved path.

7. The apparatus of claim 6, wherein a terminating surface of the distal end portion of the second optical fiber is flush with the portion of the outer surface of the member that defines the transmissive portion.

8. The apparatus of claim 6, wherein a proximal end of the second optical fiber is configured to be coupled to the laser source.

9. The apparatus of claim 1, wherein the optical fiber is a first optical fiber, the apparatus further comprising a second optical fiber, a distal end portion of the second optical fiber being disposed within the member along a second curved path.

10. The apparatus of claim 9, wherein the transmissive portion is a first transmissive portion, a terminating surface of the distal end portion of the second optical fiber is flush with a portion of the outer surface of the member that defines a second transmissive portion.

11. An apparatus, comprising:
a member having an interior defining a curved path, the member including a transmissive portion offset from a centerline of the member; and
an optical fiber having a proximal end portion and a distal end portion, the proximal end portion of the optical fiber configured to be coupled to a laser source, the distal end portion of the optical fiber being fixedly disposed within the curved path, a terminating surface of the distal end portion of the optical fiber being flush with a portion of an outer surface of the member that defines the transmissive portion; and
an outer member, the member being disposed within the outer member, the outer member having a transmissive portion and a blunt distal end, the transmissive portion of the outer member being at least partially aligned with the transmissive portion of the member.

12. The apparatus of claim 11, wherein the transmissive portion of the member includes an opening.

13. The apparatus of claim 11, wherein the optical fiber includes a core, a cladding disposed about the core, and a buffer disposed about the cladding, a distal end of the core being offset from a distal end of the cladding and a distal end of the buffer.

14. The apparatus of claim 11, wherein the optical fiber is a first optical fiber, the apparatus further comprising a second optical fiber, a distal end portion of the second optical fiber being disposed within the member along the curved path, a terminating surface of the distal end portion of the second optical fiber being flush with the portion of the outer surface of the member that defines the transmissive portion.

15. The apparatus of claim 11, wherein the optical fiber is a first optical fiber, the apparatus further comprising a second optical fiber, a distal end portion of the second optical fiber being disposed within the member along a second curved path, a terminating surface of the distal end portion of the second optical fiber being flush with a portion of the outer surface of the member that defines a second transmissive portion.

16. A method, comprising:
fixedly disposing a distal end portion of an optical fiber within a curved path defined by a member configured to be inserted into a patient's body; and
aligning a terminating surface of the distal end portion of the optical fiber flush with a portion of an outer surface of the member that defines a transmissive portion; and
an outer member, the member being disposed within the outer member, the outer member having a transmissive portion and a blunt distal end, the transmissive portion of the outer member being at least partially aligned with the transmissive portion of the member.

17. The method of claim 16, further comprising bending, before the disposing, the distal end portion of the optical fiber.

18. The method of claim 16, further comprising thermally bending, before the disposing, the distal end portion of the optical fiber.

19. The method of claim 16, wherein the curved path includes a plurality of segments.

20. The method of claim 16, wherein the optical fiber is a first optical fiber, the method further comprising:
disposing a distal end portion of a second optical fiber within the curved path of the member; and
aligning a terminating surface of the distal end portion of the second optical fiber flush with the portion of the outer surface of the member that defines the transmissive portion.

21. The method of claim 16, wherein the optical fiber is a first optical fiber, the method further comprising:
disposing a distal end portion of a second optical fiber within a second curved path defined by the member; and
aligning a terminating surface of the distal end portion of the second optical fiber flush with a portion of the outer surface of the member that defines a second transmissive portion.

22. A method, comprising:
inserting a member into a patient's body, the member having an outer surface that includes a transmissive portion, a distal end of an optical fiber being fixedly disposed within a curved path defined by the member, a terminating surface of the distal end portion of the optical fiber being flush with a portion of the outer surface of the member that defines the transmissive portion; and
after the inserting, activating a laser source to transmit laser energy to the patient's body and through the transmissive portion of the member; and
an outer member, the member being disposed within the outer member, the outer member having a transmissive portion and a blunt distal end, the transmissive portion of the outer member being at least partially aligned with the transmissive portion of the member.

23. The apparatus of claim 1, wherein the member includes a blunt distal end adjacent to the distal end of the outer member.

24. The method of claim 16, wherein the member includes a blunt distal end adjacent to the distal end of the outer member.

* * * * *